US009072450B2

(12) United States Patent
Ushijima et al.

(10) Patent No.: US 9,072,450 B2
(45) Date of Patent: Jul. 7, 2015

(54) ENDOSCOPE APPARATUS
(71) Applicant: OLYMPUS MEDICAL SYSTEMS CORP., Tokyo (JP)
(72) Inventors: Takanori Ushijima, Tama (JP); Susumu Aono, Hachioji (JP); Toshihiro Matsui, Akiruno (JP); Mitsutaka Kokubo, Hino (JP); Natsuki Hori, Hachioji (JP)
(73) Assignee: OLYMPUS MEDICAL SYSTEMS CORP., Tokyo (JP)
( * ) Notice: Subject to any disclaimer, the term of this patent is extended or adjusted under 35 U.S.C. 154(b) by 0 days.
(21) Appl. No.: 13/746,373
(22) Filed: Jan. 22, 2013
(65) Prior Publication Data
US 2013/0137925 A1 May 30, 2013

Related U.S. Application Data
(63) Continuation of application No. PCT/JP2012/059479, filed on Apr. 6, 2012.

(30) Foreign Application Priority Data

Jul. 19, 2011 (JP) ................................ 2011-158243

(51) Int. Cl.
*A61B 1/00* (2006.01)
*A61B 1/05* (2006.01)
(Continued)
(52) U.S. Cl.
CPC ............... *A61B 1/051* (2013.01); *A61B 1/0008* (2013.01); *A61B 1/05* (2013.01); *A61B 1/07* (2013.01); *A61B 1/128* (2013.01); *A61B 1/00096* (2013.01); *A61B 1/0676* (2013.01)
(58) Field of Classification Search
CPC .... A61B 1/0008; A61B 1/00096; A61B 1/05; A61B 1/06; A61B 1/12; A61B 1/128

USPC .......................................... 600/109, 129, 160
See application file for complete search history.

(56) References Cited

U.S. PATENT DOCUMENTS 3,615,366 A * 10/1971 Allen .............................. 420/42
2004/0039249 A1 * 2/2004 Shiro et al. ..................... 600/101
(Continued)

FOREIGN PATENT DOCUMENTS

JP         2000-287913      10/2000
JP         2001-046317       2/2001
(Continued)

OTHER PUBLICATIONS

Extended Supplementary European Search Report dated Mar. 17, 2015 from related European application No. 12 81 4558.8.

*Primary Examiner* — Anhtuan T Nguyen
*Assistant Examiner* — Aaron B Fairchild
(74) *Attorney, Agent, or Firm* — Scully, Scott, Murphy & Presser, P.C.

(57) ABSTRACT

A distal end barrel that holds a light guide bundle and an electronic image pickup unit inside a distal end portion is formed in such a manner that the distal end barrel is divided in a first distal end barrel arranged on the distal end side of the distal end portion and a second distal end barrel supported via the first distal end barrel so as not to be exposed at an outer surface of the distal end portion, the second distal end barrel holding the light guide bundle and the electronic image pickup unit, and the second distal end barrel includes a member having a thermal conductivity higher than the thermal conductivity of the first distal end barrel, thereby protecting the image pickup device from thermal damage without an increase in temperature of the outer surface of the distal end portion.

5 Claims, 9 Drawing Sheets

(51) Int. Cl.
*A61B 1/12* (2006.01)
*A61B 1/04* (2006.01)
*A61B 1/06* (2006.01)
*A61B 1/07* (2006.01)

(56) References Cited

U.S. PATENT DOCUMENTS

| | | | |
|---|---|---|---|
| 2006/0183977 A1* | 8/2006 | Ishigami et al. | 600/179 |
| 2007/0191684 A1 | 8/2007 | Hirata | |
| 2008/0300457 A1 | 12/2008 | Hosaka et al. | |
| 2010/0292538 A1* | 11/2010 | Hirata et al. | 600/129 |
| 2010/0309553 A1 | 12/2010 | Nagamizu | |

FOREIGN PATENT DOCUMENTS

| | | |
|---|---|---|
| JP | 2001-299677 | 10/2001 |
| JP | 2002-177197 | 6/2002 |
| JP | 2003-153852 | 5/2003 |
| JP | 2007-014488 | 1/2007 |
| JP | 2008-155016 | 7/2008 |
| JP | 2009-022636 | 2/2009 |
| JP | 2009-247620 | 10/2009 |
| JP | 2010-187902 | 9/2010 |
| JP | 2011-072424 | 4/2011 |
| WO | WO 2006/046559 A1 | 5/2006 |

* cited by examiner

ENDOSCOPE APPARATUS

CROSS REFERENCE TO RELATED APPLICATION

This application is a continuation application of PCT/JP2012/059479 filed on Apr. 6, 2012 and claims benefit of Japanese Application No. 2011-158243 filed in Japan on Jul. 19, 2011, the entire contents of which are incorporated herein by this reference.

BACKGROUND OF THE INVENTION

1. Field of the Invention

The present invention relates to an endoscope apparatus including an electronic image pickup unit at a distal end portion of an insertion portion.

2. Description of the Related Art

Conventionally, in, e.g., a medical field, in order to observe a site inside a subject where visual observation is difficult, such as an inside of a living body, an endoscope including an electronic image pickup unit for observing an optical image at a distal end portion of an insertion portion is used. The electronic image pickup unit includes, for example, an objective lens and an image pickup device such as a CCD (charge-coupled device) or CMOS (complementary metal-oxide semiconductor) sensor disposed at a plane on which an image from the objective lens is formed.

In recent years, for endoscope apparatuses of this type, enhancement in performance of an image pickup device and an increase in definition of picked up images, which is realized by an increase in output of illuminating light, have been promoted. However, for example, where performance of an image pickup device is enhanced, the amount of heat generated from the image pickup device and, e.g., various electronic components attached thereto. Furthermore, where the output of illuminating light is increased, the amount of light irregularly reflected inside the illumination optical system increases, and a majority of irregularly-reflected light is transformed into heat inside the distal end portion. Furthermore, if the heat remains inside the distal end portion, what is called temperature noise may occur in the image pickup device, resulting in image deterioration.

In response to such problems, for example, Japanese Patent Application Laid-Open Publication No. 2001-299677 discloses a technique in which a holding member that includes a stainless steel material having good thermal conductivity is housed inside a first outer case that includes a stainless steel material having good mechanical endurance and good chemical endurance (chemical resistance), an electronic image pickup unit (e.g., a light-receiving lens and a CCD) is inserted in an inner space of the holding member and a plurality of LEDs are disposed as a light source at positions surrounding the light-receiving lens at a front end face of the holding member. In the technique in Patent Literature 1, the holding member is formed using a material having high thermal conductivity, and an outer peripheral face of the holding member is brought into direct contact with an inner circumferential face of the thin-walled first outer case, whereby heat generated in the plurality of LEDs is transferred through the holding member and efficiently released to the outside from the first outer case.

SUMMARY OF THE INVENTION

An endoscope apparatus according to an aspect of the present invention provides an endoscope apparatus including a light source and an electronic image pickup unit held inside a distal end portion of an insertion portion, the endoscope apparatus including: a first distal end barrel including a front wall portion on a distal end side thereof, the first distal end barrel having a tubular shape and being disposed on a distal end side of the distal end portion; a distal end cover fitted on an outer peripheral portion of the first distal end barrel; a second distal end barrel including a member having a thermal conductivity higher than the thermal conductivity of the first distal end barrel, a distal end side of the second distal end barrel being fitted in an inner peripheral portion of the first distal end barrel at a position on a base portion side relative to the front wall portion, whereby the second distal end barrel is supported via the first distal end barrel so as not to be exposed at an outer surface of the distal end portion and so as to be spaced from the distal end cover, the second distal end barrel holding the light source and the electronic image pickup unit inside; a heat insulating portion interposed between the distal end cover and the second distal end barrel, the heat insulating portion blocking heat transfer from the second distal end barrel to the distal end cover; and a heat transfer member adhered to at least a part of the second distal end barrel so as not to be in contact with the distal end cover, the heat transfer member transferring heat from the light source and the electronic image pickup unit, the heat being absorbed by the second distal end barrel, to a base portion side of the insertion portion.

DETAILED DESCRIPTION OF THE PREFERRED EMBODIMENT

Figure 1:
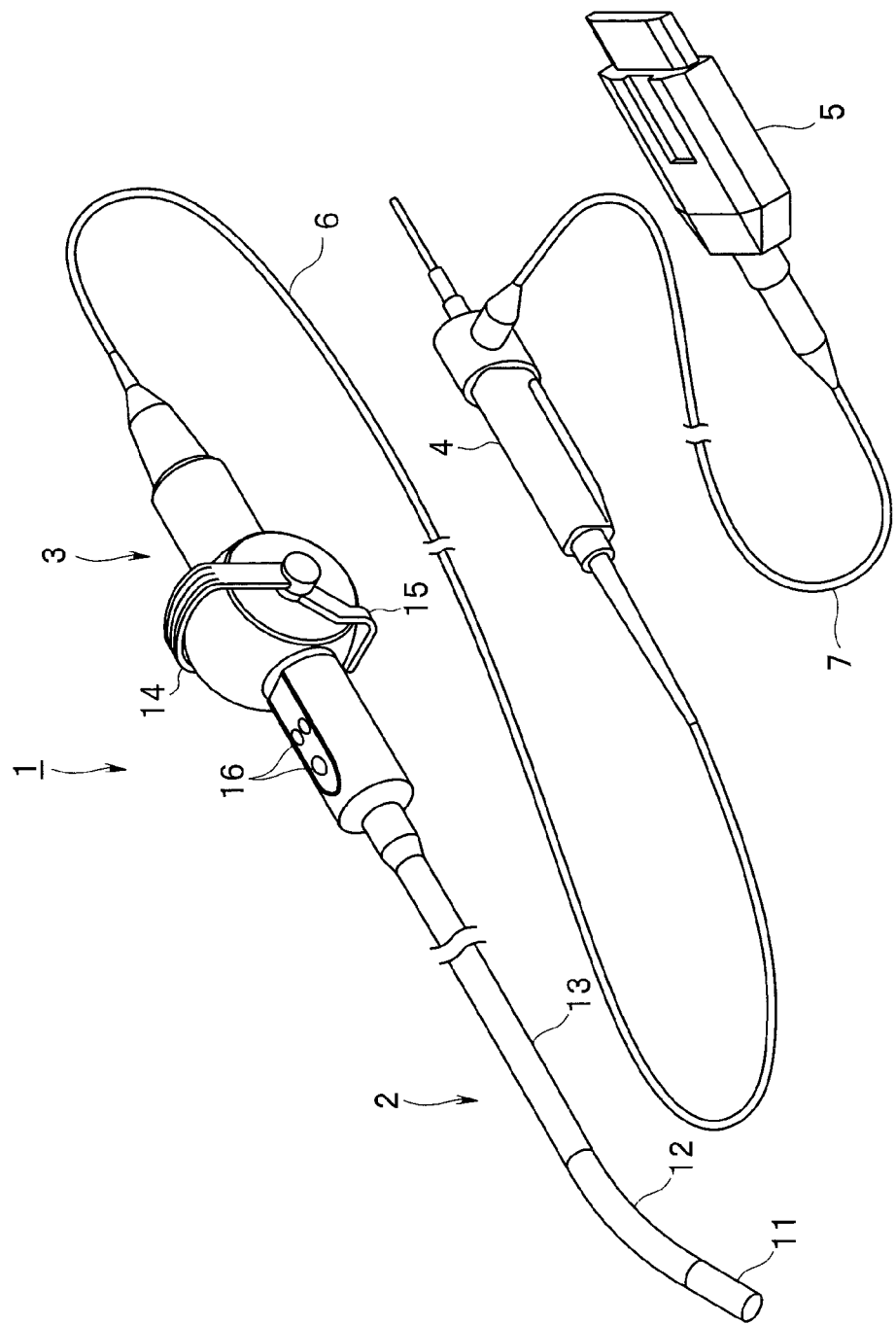
FIG. 1 is a perspective diagram illustrating an overall configuration of an endoscope apparatus.
Figure 2:
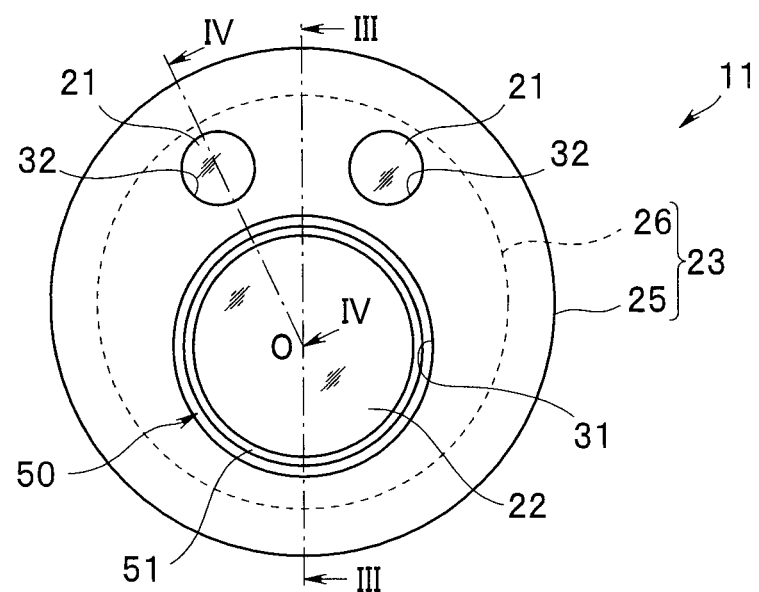
FIG. 2 is a diagram of an end face of a distal end portion of an insertion portion.
Figure 3:
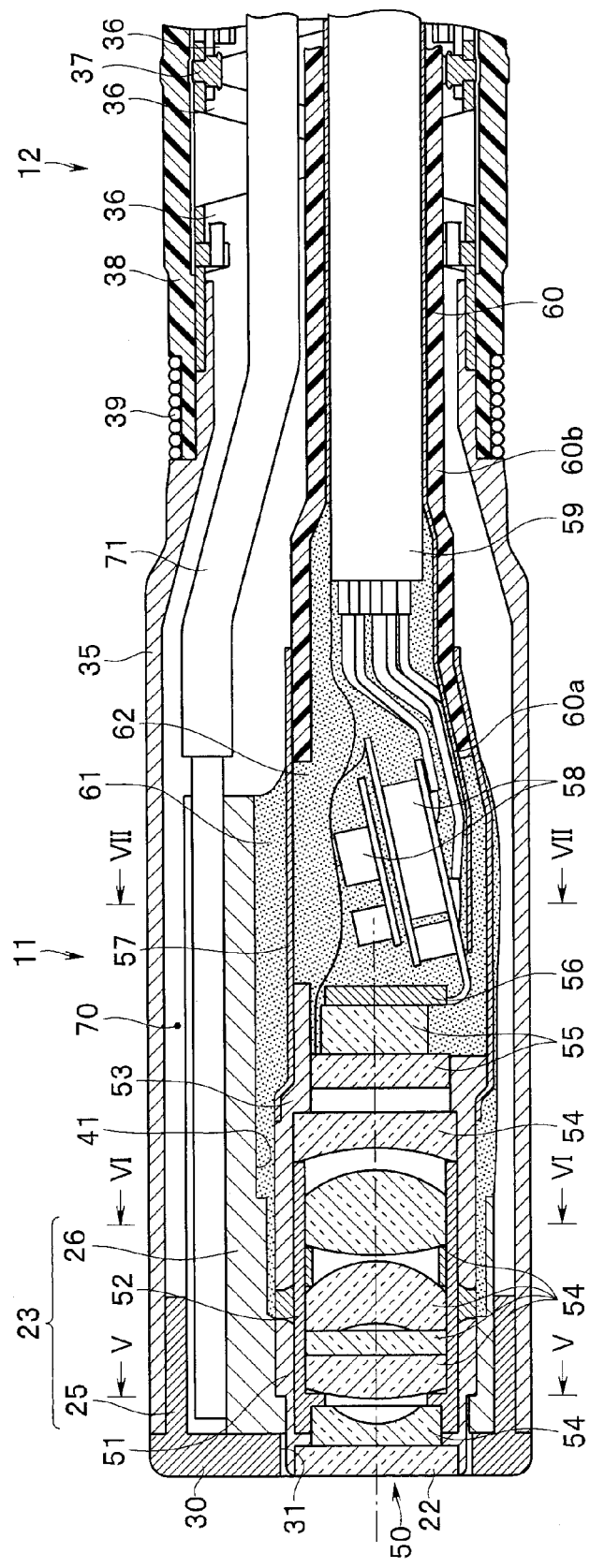
FIG. 3 is a cross-sectional view of the distal end portion along line in FIG. 2.
Figure 4:
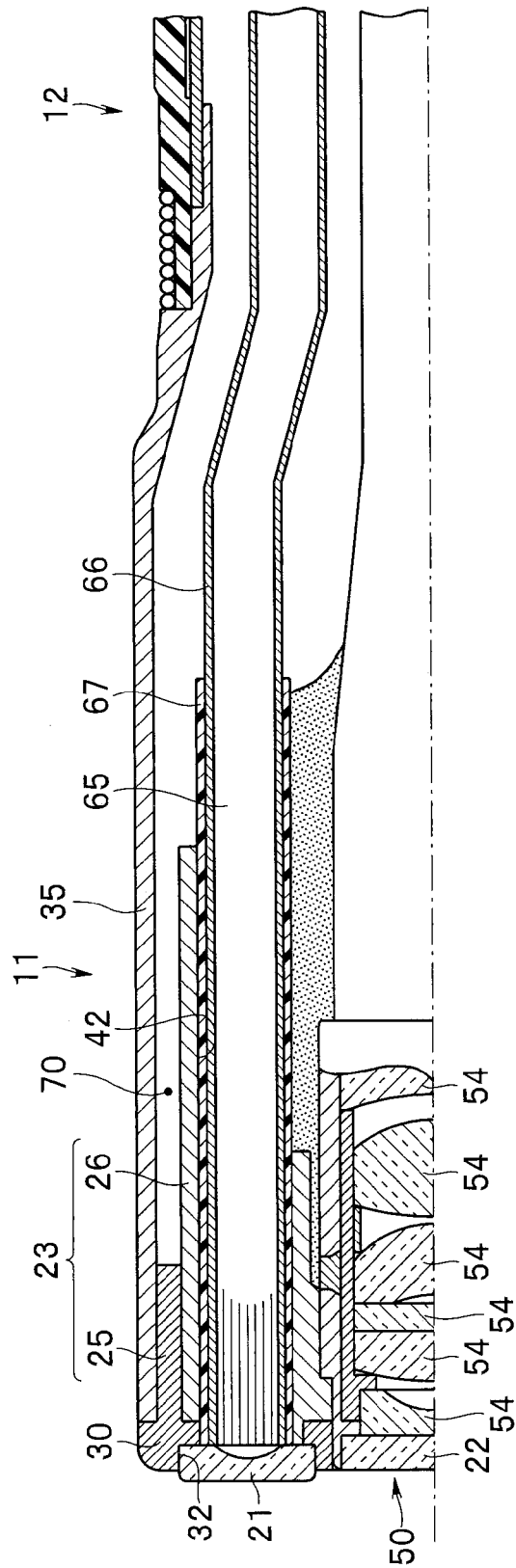
FIG. 4 is a cross-sectional view of the distal end portion along line IV-IV in FIG. 2.
Figure 5:
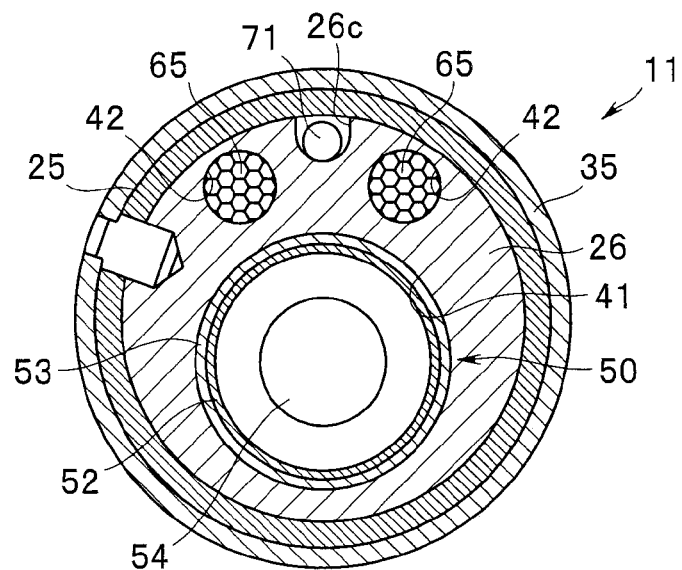
FIG. 5 is a cross-sectional view of the distal end portion along line V-V in FIG. 3.
Figure 6:
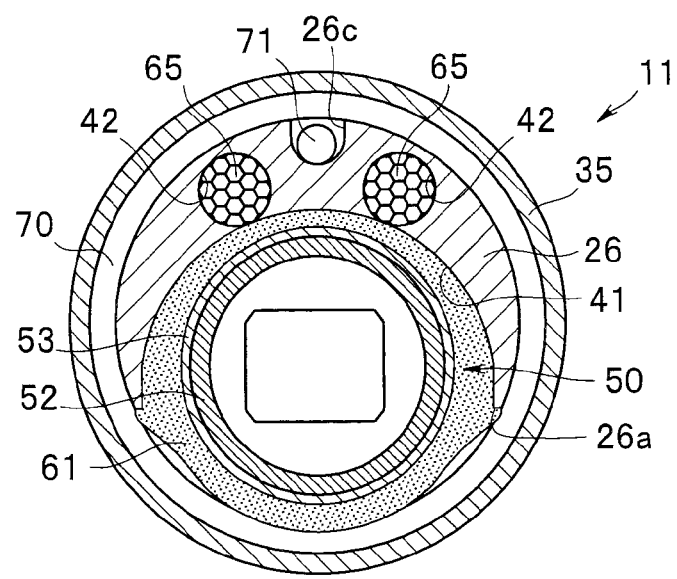
FIG. 6 is a cross-sectional view of the distal end portion along line VI-VI in FIG. 3.
Figure 7:
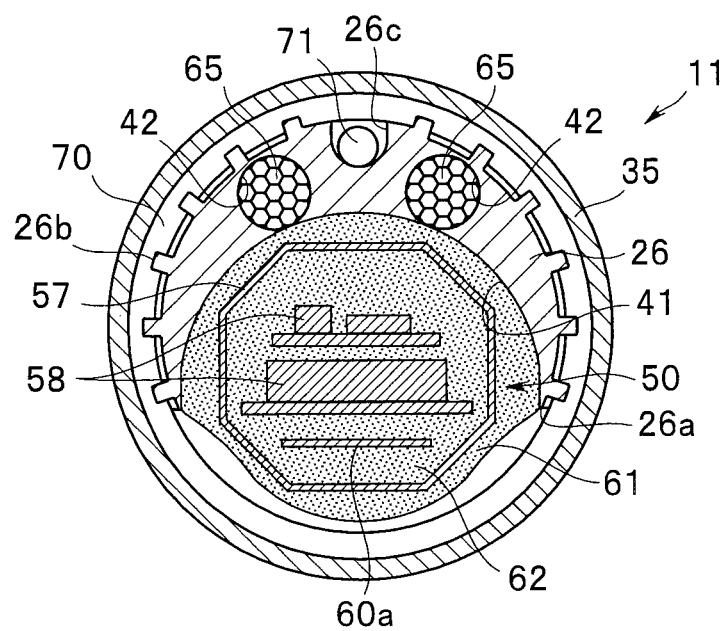
FIG. 7 is a cross-sectional view of the distal end portion along line VII-VII in FIG. 3.
Figure 8:
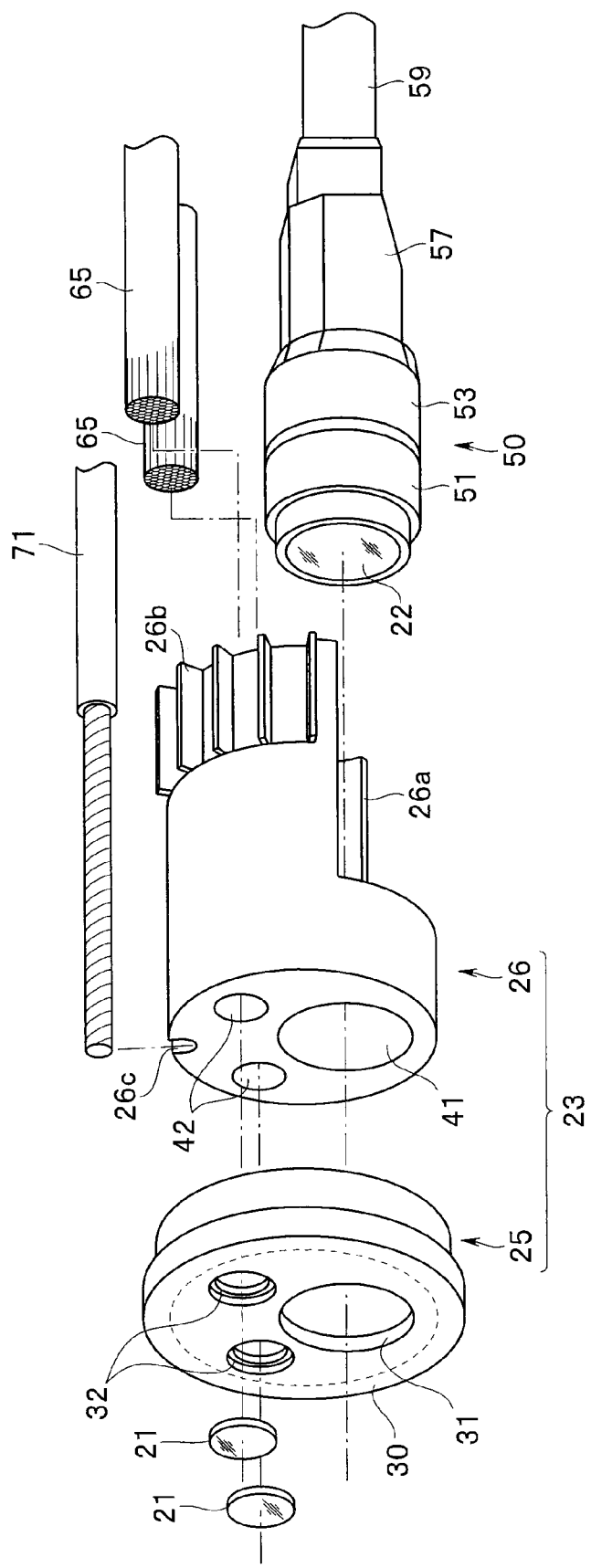
FIG. 8 is an exploded perspective diagram illustrating a main part of an inner structure of the distal end portion.

A mode of the present invention will be described below with reference to the drawings. The drawings relate to an embodiment of the present invention: FIG. 1 is a perspective diagram illustrating an overall configuration of an endoscope apparatus; FIG. 2 is a diagram of an end face of a distal end portion of an insertion portion; FIG. 3 is a cross-sectional view of the distal end portion along line in FIG. 2; FIG. 4 is a cross-sectional view of the distal end portion along line IV-IV in FIG. 2; FIG. 5 is a cross-sectional view of the distal end portion along line V-V in FIG. 3; FIG. 6 is a cross-sectional view of the distal end portion along line VI-VI in FIG. 3; FIG. 7 is a cross-sectional view of the distal end portion along line VII-VII in FIG. 3; and FIG. 8 is an exploded perspective diagram illustrating a main part of an inner structure of the distal end portion.

As illustrated in FIG. 1, an endoscope apparatus 1 mainly includes an elongated insertion portion 2, an operation section 3 provided so as to be continuous with a proximal end of the insertion portion 2, a light guide connector 4 connected to a non-illustrated light source apparatus, and a video connector 5 connected to a non-illustrated video system center. Note that in the endoscope apparatus 1, the operation section 3 and the light guide connector 4 are connected via a flexible cable 6, and the light guide connector 4 and the video connector 5 are connected via a communication cable 7.

In the insertion portion 2, a distal end portion 11 mainly including a metal member, a bending portion 12, and a rigid tube 13, which is a metal tube of, e.g., a stainless steel, are provided so as to be continuous from one to another in this order from the distal end side. The insertion portion 2 is a part to be inserted into a body, and incorporates, e.g., a cable and light guides, which will be described later, in its inside.

The operation section 3 includes angle levers 14 and 15 for remotely operating the bending portion 12, and various switches 16 for operating, e.g., the light source apparatus and the video system center. The angle levers 14 and 15 are bending operation means enabling the bending portion 12 of the insertion portion 2 to be operated in four directions, upward, downward, leftward and rightward. Note that although the endoscope apparatus 1 according to the present embodiment is, for example, a rigid endoscope apparatus in which a majority of the insertion portion 2 except the bending portion 12 is rigid, an endoscope to which the present invention can be applied is not limited to this example, and may be, for example, a flexible endoscope apparatus in which a part of the insertion portion 2 on the base portion side relative to the bending portion 12 is flexible.

Next, an inner configuration of a distal end of the insertion portion 2 of the endoscope apparatus 1 will be described in details with reference to FIGS. 2 to 8.

As illustrated in FIG. 2, at an end face (distal end face) of the distal end portion 11 of the endoscope apparatus 1, illumination lenses 21, which serve as illumination windows for illumination, a transparent cover member 22 for an optical member, the transparent cover member 22 serving as an observation window for image pickup, are disposed so as to be exposed. Note that the endoscope apparatus 1 according to the present embodiment includes two illumination lenses 21 at a front face of the distal end portion 11.

For more detailed description, as illustrated in FIGS. 3 to 8, the distal end portion 11 of the insertion portion 2 includes a distal end barrel (distal end rigid portion) 23. The distal end barrel 23 is formed in such a manner that the distal end barrel 23 is divided in a first distal end barrel 25 disposed on the distal end side (more specifically, a distalmost end portion) of the distal end portion 11, and a second distal end barrel 26 disposed behind the first distal end barrel 25.

The first distal end barrel 25 includes, for example, a substantially-cylindrical member including a metal material having low thermal conductivity such as a stainless steel-based metal.

On the distal end side of the first distal end barrel 25, a front wall portion 30 having a substantially-discoid shape is formed, and in the front wall portion 30, an observation hole 31 opens. Furthermore, in the front wall portion 30, a pair of lens holding holes 32 open at respective positions that are offset from the observation hole 31, and the illumination lenses 21 are fitted and thereby held in the respective lens holding holes 32. On the other hand, the base portion side of the first distal end barrel 25 is fitted and thereby fixed in a distal end cover 35 that, for example, includes a metal and has a substantially-cylindrical shape.

Here, a bending piece positioned at a frontmost position from among a plurality of bending pieces 36 aligned inside the bending portion 12 is joined to a base portion of the distal end cover 35. In the bending pieces 36, bending pieces adjacent to one another are pivotally joined via axial rivets 37. Outer peripheries of the bending pieces 36 joined as described above are integrally covered by a flexible tube 38 including, e.g., fluorine-contained rubber. An outer peripheral portion of a distal end of the flexible tube 38 is connected to the proximal end of the distal end cover 35 via a winding adherence portion 39.

A second distal end barrel 26 includes, for example, a substantially-columnar member including a metal material having high thermal conductivity such as a copper-based metal or an aluminum-based metal.

In the second distal end barrel 26, a unit holding hole 41 opens at a position corresponding to the observation hole 31 of the first distal end barrel 25, and an electronic image pickup unit 50 is held in the unit holding hole 41. Furthermore, in the second distal end barrel 26, light guide holding holes 42 open at respective positions corresponding to the respective lens holding holes 32 in the first distal end barrel 25, and the distal end side of a light guide bundle 65, which serves as a light source, is held in each of the light guide holding holes 42.

For detailed description, as illustrated in FIG. 3, the electronic image pickup unit 50 includes a support barrel 51 that holds the transparent cover member 22 as a result of the transparent cover member 22 being fitted in the support barrel 51. The support barrel 51 includes a metal member having a substantially-cylindrical shape, and is fitted and thereby fixed in the distal end side of the unit holding hole 41 that opens in the second distal end barrel 26. Furthermore, inside the unit holding hole 41, a lens holding barrel 52 is fitted in the support barrel 51, and a unit holding barrel 53 is further fitted on the lens holding barrel 52.

A plurality of optical lenses 54 are fitted and held in the lens holding barrel 52 and the unit holding barrel 53, and the optical lens 54 and the transparent cover member 22 form an objective optical system. Furthermore, behind the objective optical system, a cover glass 55 is fitted and held in the unit holding barrel 53, and an image pickup device 56 including, e.g., a CCD or a CMOS is held on the cover glass 55. Furthermore, an image pickup section sheathing barrel 57 including a sheet metal is joined to a proximal end portion of the unit holding barrel 53, and inside the image pickup section sheathing barrel 57, various electronic components 58 attached to the image pickup device 56 are housed in such a manner that the electronic components 58 are modularized together with the image pickup device 56.

The electronic image pickup unit 50 configured as described above is held in the second distal end barrel 26 mainly through the support barrel 51, the lens holding barrel 52 and the unit holding barrel 53 in such a manner that heat can be transferred. Note that although use of a resin for the unit holding barrel 53 enables insulation between the first metal barrel 25 and the distal end cover 35, which are outer layer metals, and the image pickup device 56, in such case, also, heat can be transferred between the lens holding barrel 52 and the second distal end barrel 26.

Here, a distal end portion of a signal cable 59 extending from the operation section 3 side is joined to the proximal end side of the image pickup section sheathing barrel 57, and is thereby electrically connected to the various electronic components 58. In the present embodiment, on an outer periphery of the signal cable 59, for example, a heat-transfer tube 60 including a copper mesh tube is provided, and a reed-shaped heat-transfer strip 60a formed on the distal end side of the heat-transfer tube 60 is provided so as to extend inside the image pickup section sheathing barrel 57 and face the vicinity of the various electronic components 58. The distal end portion of the signal cable 59 and the outside of the heat-transfer tube 60 are sheathed by, for example, a coat member 60b including a heat shrinkable tube.

Furthermore, on the base portion side of the second distal end barrel 26, a cut portion 26a that releases a part of the unit holding hole 41 is formed (see FIG. 8), and through the cut portion 26a, an adhesive 61 is charged inside the unit holding hole 41. Furthermore, an adhesive 62 is also charged inside the image pickup section sheathing barrel 57, and consequently, the electronic image pickup unit 50 is enclosed in a liquid-tight manner inside the second distal end barrel 26, and heat can be transferred from the electronic image pickup unit 50 to the second distal end barrel 26 also through the adhesives. Note that arrangement of a part of the electronic image pickup unit 50, the part having a large outer diameter in the cut portion 26a enables reduction in outer diameter of the insertion portion of the endoscope and provision of a later-described heat-insulating layer 70 with the reduced outer diameter of the insertion portion kept.

As illustrated in FIG. 4, the distal end sides of the respective light guide bundles 65 are fitted and fixed inside the respective light guide holding holes 42.

Here, heat generated in the distal end sides of the light guide bundles 65 is basically diffused to the second distal end barrel 26 through the light guide holding holes 42; however, in order to suppress the amount of heat diffused to the second distal end barrel 26 while a capability of cooling of the light guide bundles 65 is secured, for example, as illustrated in FIG. 4, for example, a heat-transfer tube 66 including, e.g., a copper mesh tube is desirably provided on an outer periphery of each of the light guide bundles 65. Furthermore, on the distal end side of each light guide bundle 65, a tubular member 67 including, e.g., a resin having a heat-insulating property or silicon is desirably provided on an outer periphery of the heat-transfer tube 66.

As described above, the second distal end barrel 26 holding the electronic image pickup unit 50 and the light guide bundle 65 is fitted in the base portion side of the first distal end barrel 25 inside the distal end cover 35, and fixed to the first distal end barrel 25 via non-illustrated fixing pins. Consequently, the second distal end barrel 26 is supported via the first distal end barrel 25 in such a manner that the second distal end barrel 26 is not exposed at an outer surface of the distal end portion 11. In such case, if the fixing pins are used also for fixing the electronic image pickup unit 50 and the second distal end barrel to each other, the number of fixing pins can be reduced and thus a larger volume of the distal end barrel 26 can be secured. A hole allowing a heat transfer member 71 to be inserted therethrough can be provided in the distal end barrel 26: in the example illustrated in FIG. 3, the hole is formed as a recessed groove 26c. Furthermore, in order to promote heat transfer between the heat transfer member 71 and the second distal end barrel 26, it is desirable that a distance of a joint between the heat transfer member 71 and the second distal end barrel 26 be as long as possible.

In such case, alignment of the observation hole 31 and the lens holding holes 32 in the first distal end barrel 25 and the unit holding hole 41 and the light guide holding holes 42 in the second distal end barrel 26 allows the transparent cover member 22 positioned at a distal end of the electronic image pickup unit 50 to be exposed to the outside via the observation hole 31 and also allows the distal end sides of the respective light guide bundles 65 to be optically connected to the respective illumination lenses 21.

Furthermore, the second distal end barrel 26 is held so as not to be in contact with the distal end cover 35, and consequently, between the second distal end barrel 26 and the distal end cover 35, a heat-insulating layer 70 including an air space is formed (see FIGS. 3, 6 and 7). Furthermore, in the present embodiment, in an outer periphery of the base portion side of the second distal end barrel 26, a plurality of radiation fins 26b exposed in the heat-insulating layer 70 (air space) are provided (see FIGS. 7 and 8). Note that although not illustrated, the heat-insulating layer 70 can include, e.g., a heat-insulating member instead of an air space.

Furthermore, the distal end side of the heat transfer member 71 that transfers heat of the second distal end barrel 26 to the base portion side of the insertion portion 2 is adhered to a part of an outer peripheral face of the second distal end barrel 26. As illustrated in FIG. 3, for the heat transfer member 71, for example, a known insulated electric wire can be employed, and thermal connection of the heat transfer member 71 to the second distal end barrel 26 is provided, for example, by arranging a part of the distal end side of the insulated electric wire, the part being exposed from an outer coat of the insulated electric wire, in the recessed groove 26c formed at a part of the outer peripheral face of the second distal end barrel 26 and fixing the heat transfer member 71 to the second distal end barrel 26 via, e.g., an adhesive or solder. In this case, the heat transfer member 71 is desirably adhered to the second distal end barrel 26 in such a manner that the heat transfer member 71 is not in contact with the distal end cover 35. Furthermore, although the heat transfer member 71 is not necessarily an insulated electric wire for thermal conductivity, the heat transfer member 71 is desirably a coated one for protection of the electric wire when the heat transfer member 71 is bent and prevention of interference between the heat transfer member 71 and the other incorporated members. The number of heat transfer members is not limited to one and a plurality of heat transfer members may be included. Furthermore, the heat transfer member 71 may have a branched shape in a layout of the inside of the bending portion and the insertion portion. The heat transfer member 71 includes, e.g., a silver solder wire, a copper-tin wire or a copper wire.

According to such embodiment, the distal end barrel 23 that holds the light guide bundles 65 and the electronic image pickup unit 50 inside the distal end portion 11 is formed in such a manner that the distal end barrel 23 is divided in the first distal end barrel 25 arranged on the distal end side of the distal end portion 11 and the second distal end barrel 26 supported via the first distal end barrel 25 so as not to be exposed at the outer surface of the distal end portion 11, the second distal end barrel 26 holding the light guide bundle 65 and the electronic image pickup unit 50, and the second distal end barrel 26 includes a member having a thermal conductivity higher than the thermal conductivity of the first distal end barrel 25, enabling protection of the image pickup device 56 from thermal damage without an increase in temperature of the outer surface of the distal end portion 11.

In other words, as a result of the second distal end barrel 26 including a member having high thermal conductivity and the light guide bundles 65 and the electronic image pickup unit 50 being held in the second distal end barrel 26, heat generated in the light guide bundle 65 and the electronic image pickup unit 50 can be diffused to the second distal end barrel 26 side, enabling protection of the image pickup device 56 from thermal damage. In addition, as a result of the second distal end barrel 26 being arranged so as not to be exposed at the outer surface of the distal end portion 11 and being supported in the distal end portion 11 via the first distal end barrel 25 having a thermal conductivity lower than the thermal conductivity of the second distal end barrel 26, diffusion of heat diffused to the second distal end barrel 26 to the outer surface side of the distal end portion 11 can be suppressed. In such case, the front wall portion 30 of the first distal end barrel 25, to which a distal end face of the second distal end barrel 26 abuts, is made to be thick, enabling proper suppression of diffusion of heat from the second distal end barrel 26 side to the outer surface through the first distal end barrel 25.

In such case, the heat transfer member 71 extending on the proximal end side of the insertion portion 2 is adhered to at least a part of the second distal end barrel 26, enabling heat diffused in the second distal end barrel 26 to be favorably released via the heat transfer member 71. Accordingly, even where the amount of heat generated in the light guide bundles 65 and the electronic image pickup unit 50 is large, the image pickup device 56 can more properly be protected from thermal damage while an increase in temperature of the outer surface of the distal end portion 11 can be suppressed. Note that as illustrated in FIGS. 5 to 8, provision of the heat transfer member 71 at a position between the light guide bundles 65 and opposed to the image pickup unit 50 provides more favorable balancing of incorporated members inside the bending portion, enabling smoother behavior of the incorporated members during bending.

Furthermore, the heat-insulating layer 70 is interposed between the distal end cover 35, which forms the outer surface of the distal end portion 11, and the second distal end barrel 26, enabling more proper suppression of an increase in temperature of the outer surface of the distal end portion 11. In such case, in particular, where the heat-insulating layer 70 includes an air space, heat transfer from the second distal end barrel 26 to the outer surface of the distal end portion 11 can be suppressed with a simple configuration without complication of the structure. In addition, provision of the radiation fins 26b exposed in the heat-insulating layer 70 (air space) on the base portion side of the second distal end barrel 26 allows heat of the second distal end barrel 26 to be efficiently diffused to the air space, enabling more favorable protection of the image pickup device 56 from thermal damage.

Where, e.g., the light guide bundles 65 are used for light sources, loss in illuminating light occurs mainly due to, e.g., irregular reflection of light at parts of connection with the respective illumination lenses 21. In addition, a majority of light subjected to, e.g., irregular reflection is transformed to heat. Accordingly, in order to suppress heat generated in the light guide bundles 65, it is desirable to enhance an efficiency of light transmission between the light guide bundles 65 and the illumination lenses 21. First to fourth modifications, which are illustrated in FIGS. 9 to 12, are each described in terms of a configuration for reduction of loss in illuminating light, and each of FIGS. 9 to 12 is a cross-sectional view of a main part of a distal end portion according to the respective modification.

Figure 9:
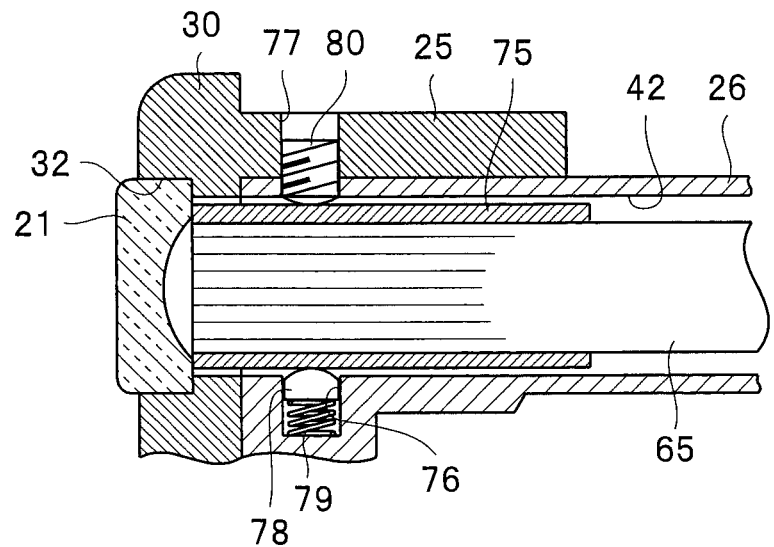
FIG. 9 is a cross-sectional view of a main part indicating a first modification of a relationship between a light guide bundle and an illumination lens.

The first modification illustrated in FIG. 9 is one intended to make optical axes of a light guide bundle 65 and an illumination lens 21 precisely correspond to each other to reduce loss in light by making a position of the light guide bundle 65 relative to the illumination lens 21 adjustable. In the first modification, a tube sleeve 75 is fixedly provided on the distal end side of the light guide bundle 65, and the light guide bundle 65 is loosely fitted in the light guide holding hole 42 via the tube sleeve 75.

Furthermore, the light guide holding hole 42 is in communication with a spring holding hole 76 that opens to a second distal end barrel 26 and a screw hole 77 extending through first and second distal end barrels 25 and 26. Inside the spring holding hole 76, a spring 79 that biases a peripheral face of the tube sleeve 75 in a predetermined direction via a pressing member 78 is housed. Furthermore, in the screw hole 77, a screw member 80 for pressing the peripheral face of the tube sleeve 75 against a biasing force of the spring 79 is threadably fitted. In the present modification, adjustment of the amount of the thread fit of the screw member 80 in the screw hole 77 enables fine adjustment of the position (e.g., the optical axis) of the light guide bundle 65 relative to the illumination lens 21.

Figure 10:
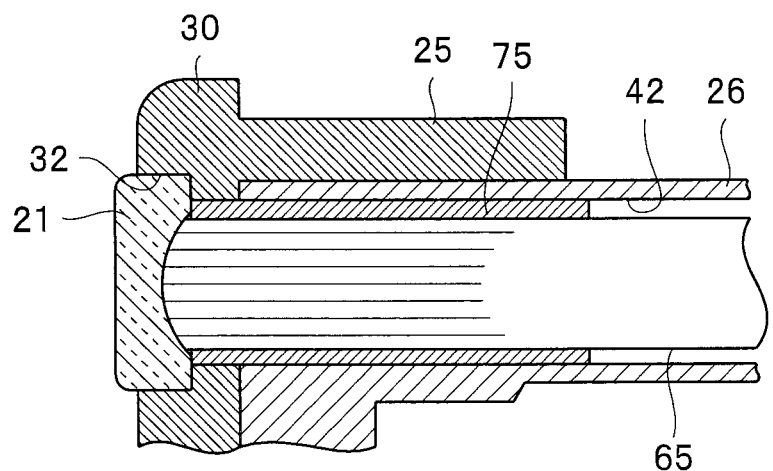
FIG. 10 is a cross-sectional view of a main part indicating a second modification of a relationship between a light guide bundle and an illumination lens.
Figure 11:
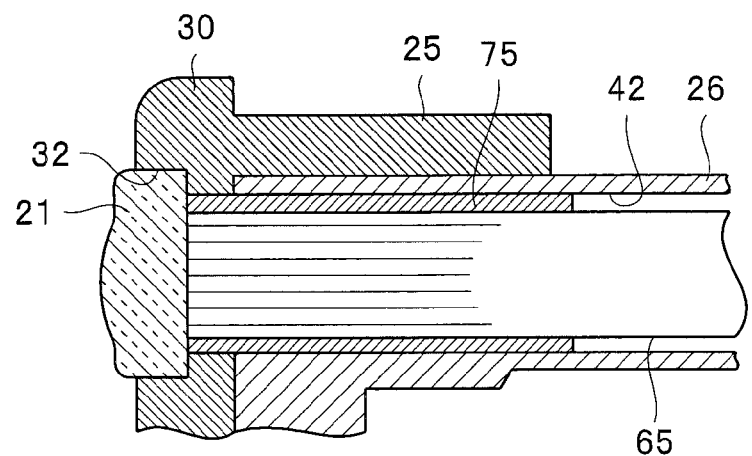
FIG. 11 is a cross-sectional view of a main part indicating a third modification of a relationship between a light guide bundle and an illumination lens.

Next, the second and third modifications illustrated in FIGS. 10 and 11 are ones each intended to reduce loss in light by bringing a distal end face of a light guide bundle 65 into close contact with a back face of an illumination lens 21.

As a configuration for bringing the light guide bundle 65 into the close contact, in the second modification illustrated in FIG. 10, the distal end face of the light guide bundle 65 is formed so as to have a shape corresponding to a curved surface of the illumination lens 21 by means of, e.g., grinding.

Furthermore, in the third modification illustrated in FIG. 11, the back face of the illumination lens 21 is formed so as to be a flat surface corresponding to the distal end face of the light guide bundle 65.

In the second and third modifications, the above configurations enable the light guide bundle 65 to be brought into close contact with the illumination lens 21, enabling reduction of loss in light.

Figure 12:
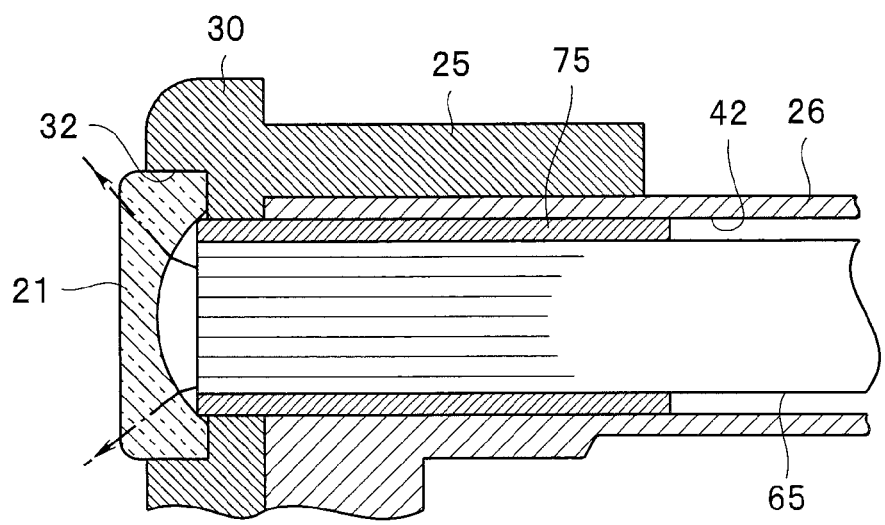
FIG. 12 is a cross-sectional view of a main part indicating a fourth modification of a relationship between a light guide bundle and an illumination lens.

Next, the fourth modification illustrated in FIG. 12 is one intended to reduce loss in light by optimizing a relationship between a curvature of an illumination lens 21 and a numerical aperture of an elemental wire included in a light guide bundle 65.

As illustrated in FIG. 12, in the present modification, the curved surface of the illumination lens 21 is designed based on the relationship with the numerical aperture of the elemental wire in the light guide bundle 65, and consequently, is designed so that light falling on a back face of the illumination lens 21 from the light guide bundle 65 does not exit from a side face (peripheral face) of the illumination lens 21 via, e.g., refraction.

Such configuration enables light falling on the back face side of the illumination lens 21 from the light guide bundle 65 to efficiently exit from the distal end face side of the illumination lens 21, enabling reduction of loss in light.

What is claimed is:
1. An endoscope apparatus comprising:
an insertion portion configured to be inserted into an interior of a subject, wherein the insertion portion has a distal end and a proximal end along a longitudinal axis, wherein the insertion portion comprises:
an outer cover extending along the longitudinal axis, wherein the outer cover has an outer cover internal surface forming an outer cover lumen;
an inner barrel extending along the longitudinal axis, wherein the inner barrel has an inner barrel external surface, and the inner barrel is arranged within the outer cover lumen such that the inner barrel external surface is spaced apart from the outer cover internal surface in a radial direction of the longitudinal axis to form an air space, wherein the inner barrel has an inner barrel internal surface forming an inner barrel lumen configured to have a heat generating element arranged therein, and wherein the inner barrel has a first thermal conductivity for conducting heat generated by the heat generating element from the inner barrel internal surface to the inner barrel external surface;

an outer barrel connecting the outer cover and the inner barrel, wherein the outer barrel has a second thermal conductivity lower than the first thermal conductivity, and wherein the outer barrel and the outer cover insulate the inner barrel from contact with the interior of the subject; and a heat transfer material in thermal contact with the inner barrel and not in direct mechanical contact with the outer cover, wherein the heat transfer material has a third thermal conductivity higher than the second thermal conductivity such that the heat conducted by the inner barrel to the inner barrel external surface is transferred to the heat transfer material.

2. The endoscope apparatus according to claim 1, wherein the inner barrel external surface is formed to have at least one radiation fin exposed in the air space.

3. The endoscope apparatus according to claim 1, wherein the outer barrel is formed of a stainless steel-based metal, and wherein the inner barrel is formed of a copper-based metal or an aluminum-based metal.

4. The endoscope apparatus according to claim 1, wherein the inner barrel and the outer barrel are arranged coaxially.

5. The endoscope apparatus according to claim 1, wherein a part of the heat transfer material is adhered to the inner barrel external surface to be in thermal contact with the inner barrel, and wherein the part of the heat transfer material adhered to the inner barrel external surface is arranged in the air space formed between the inner barrel external surface and the outer cover internal surface.

\* \* \* \* \*